(12) United States Patent
Matthiassen et al.

(10) Patent No.: US 9,585,784 B2
(45) Date of Patent: Mar. 7, 2017

(54) CATHETER ACTIVATION BY HANDLE REMOVAL

(75) Inventors: Benny Matthiassen, Lyngby (DK); Bo Kjaer Vigant Lorentsen, Helsingoer (DK); Helle Haraldsted, Glostrup (DK); Stephen Glibbery, Hellerup (DK)

(73) Assignee: Coloplast A/S, Humlebaek (DK)

( * ) Notice: Subject to any disclaimer, the term of this patent is extended or adjusted under 35 U.S.C. 154(b) by 282 days.

(21) Appl. No.: 14/241,669

(22) PCT Filed: Aug. 28, 2012

(86) PCT No.: PCT/DK2012/050312
§ 371 (c)(1),
(2), (4) Date: Feb. 27, 2014

(87) PCT Pub. No.: WO2013/029620
PCT Pub. Date: Mar. 7, 2013

(65) Prior Publication Data
US 2014/0194841 A1    Jul. 10, 2014

(30) Foreign Application Priority Data

Aug. 29, 2011    (DK) ................................ 2011 70471

(51) Int. Cl.
*A61M 25/00*    (2006.01)
*A61M 39/00*    (2006.01)
(Continued)

(52) U.S. Cl.
CPC ......... *A61F 5/4404* (2013.01); *A61M 25/002* (2013.01); *A61M 25/0017* (2013.01);
(Continued)

(58) Field of Classification Search
CPC ........ A61M 25/002; A61M 2025/0175; A61M 2039/222; A61M 2202/0496;
(Continued)

(56) References Cited

U.S. PATENT DOCUMENTS 1,581,508 A    4/1926  Bomhard
2,856,932 A    10/1958 Griffitts
(Continued)

FOREIGN PATENT DOCUMENTS

CA    1044549 A1    12/1978
CA    1187367 A1    5/1985
(Continued)

OTHER PUBLICATIONS

Bersten, A.D. et al, "Central Venous Catheter Stiffness and its Relation to Vascular Perforation", Anaesth Intens Care, vol. 16, 1986, pp. 342-357.
(Continued)

*Primary Examiner* — Adam Marcetich
(74) *Attorney, Agent, or Firm* — Coloplast Corp., Coloplast A/S; Nick Baumann (57) ABSTRACT

The invention relates to a catheter kit comprising a catheter and a urine bag stored in a package wherein flow is prevented between the catheter and urine bag when stored but enabled when the kit is used.

11 Claims, 7 Drawing Sheets

(51) Int. Cl.
*A61F 5/44* (2006.01)
*A61M 25/01* (2006.01)
*B65D 47/24* (2006.01)

(52) U.S. Cl.
CPC ..... *A61M 25/0043* (2013.01); *A61M 25/0111* (2013.01); *A61M 2025/0004* (2013.01); *A61M 2025/0006* (2013.01); *A61M 2025/0175* (2013.01); *A61M 2202/0496* (2013.01); *A61M 2210/1089* (2013.01); *B65D 47/245* (2013.01)

(58) Field of Classification Search
CPC .. A61M 2210/1085; A61M 2210/1089; A61M 25/0017; A61M 25/01; A61M 25/0111; A61M 25/0113; A61M 39/22; A61M 39/221; A61M 5/002; A61M 25/0043; A61M 2025/0004; A61M 2025/0006; A61F 5/4404; A61F 5/4405; A61B 2050/3006; A61B 2050/3013; A61B 50/30; A61J 1/10; A61J 1/14; A61J 1/1412; B65D 47/245; B65D 47/246; B65D 47/247
See application file for complete search history.

(56) References Cited

U.S. PATENT DOCUMENTS

| | | |
|---|---|---|
| 3,154,080 A | 10/1964 | Rowan et al. |
| 3,186,410 A | 6/1965 | Buono |
| 3,332,424 A | 7/1967 | Minteer |
| 3,335,723 A | 8/1967 | Waldman, Jr. et al. |
| 3,537,451 A | 11/1970 | Beck et al. |
| 3,556,294 A | 1/1971 | Walck, III et al. |
| 3,606,889 A | 9/1971 | Arblaster |
| 3,648,704 A | 3/1972 | Jackson |
| 3,661,153 A | 5/1972 | Polk et al. |
| 3,693,783 A * | 9/1972 | Hart ............... A61M 3/0262 206/210 |
| 3,750,875 A | 8/1973 | Juster |
| 3,769,981 A | 11/1973 | McWhorter |
| 3,782,381 A | 1/1974 | Winnie |
| 3,853,130 A | 12/1974 | Sheridan |
| 3,854,483 A | 12/1974 | Powers |
| 3,865,666 A | 2/1975 | Shoney |
| 3,867,945 A | 2/1975 | Long |
| 3,894,540 A | 7/1975 | Bonner, Jr. et al. |
| 3,898,993 A | 8/1975 | Taniguchi |
| 3,901,965 A | 8/1975 | Honeyman, III |
| 3,934,721 A | 1/1976 | Juster et al. |
| 3,947,175 A | 3/1976 | Melcher |
| 4,026,298 A | 5/1977 | Grausz |
| 4,041,122 A | 8/1977 | Quick et al. |
| 4,043,345 A | 8/1977 | Kramann et al. |
| 4,055,179 A * | 10/1977 | Manschot ............ A61F 5/4405 251/333 |
| 4,062,363 A | 12/1977 | Bonner, Jr. |
| 4,122,591 A | 10/1978 | Kramann et al. |
| 4,140,127 A | 2/1979 | Cianci et al. |
| 4,149,695 A | 4/1979 | Quick et al. |
| 4,188,954 A | 2/1980 | Patel et al. |
| 4,204,527 A | 5/1980 | Wu et al. |
| 4,235,232 A | 11/1980 | Spaven et al. |
| 4,246,909 A | 1/1981 | Wu et al. |
| 4,284,459 A | 8/1981 | Patel et al. |
| 4,363,406 A | 12/1982 | Salvadori |
| 4,421,509 A | 12/1983 | Schneider et al. |
| 4,455,882 A * | 6/1984 | Torii ............... A61B 5/20 138/89 |
| 4,500,313 A | 2/1985 | Young |
| 4,511,358 A | 4/1985 | Johnson, Jr. et al. |
| 4,551,292 A | 11/1985 | Fletcher et al. |
| 4,553,959 A | 11/1985 | Hickey et al. |
| 4,583,967 A | 4/1986 | Harris |
| 4,588,160 A | 5/1986 | Flynn et al. |
| 4,601,713 A | 7/1986 | Fuqua |
| 4,615,472 A | 10/1986 | Nash |
| 4,652,259 A | 3/1987 | O'Neil |
| 4,673,161 A | 6/1987 | Flynn et al. |
| 4,743,236 A | 5/1988 | Manschot |
| 4,750,877 A | 6/1988 | McFarlane |
| 4,802,650 A | 2/1989 | Stricker |
| 4,805,611 A | 2/1989 | Hodgkins |
| 4,811,847 A | 3/1989 | Reif et al. |
| 4,850,350 A | 7/1989 | Jackson |
| 4,863,441 A | 9/1989 | Lindsay et al. |
| 4,871,358 A | 10/1989 | Gold |
| 4,957,682 A | 9/1990 | Kobayashi et al. |
| 5,035,399 A | 7/1991 | Rantanen-Lee |
| 5,041,085 A | 8/1991 | Osborne et al. |
| 5,145,094 A * | 9/1992 | Perlmutter ............ B65D 50/06 215/311 |
| 5,147,341 A | 9/1992 | Starke et al. |
| 5,167,646 A | 12/1992 | Swafford |
| 5,167,647 A | 12/1992 | Wijkamp et al. |
| 5,183,470 A | 2/1993 | Wettermann |
| RE34,223 E | 4/1993 | Bonaldo |
| 5,242,398 A | 9/1993 | Knoll et al. |
| 5,263,946 A | 11/1993 | Klug |
| 5,290,229 A | 3/1994 | Paskar |
| 5,320,613 A | 6/1994 | Houge et al. |
| 5,354,263 A | 10/1994 | Coll |
| 5,391,155 A | 2/1995 | Sachse |
| 5,409,469 A | 4/1995 | Schaerf |
| 5,454,798 A | 10/1995 | Kubalak et al. |
| 5,489,256 A | 2/1996 | Adair |
| 5,510,065 A | 4/1996 | McFarlane |
| 5,531,717 A | 7/1996 | Roberto et al. |
| 5,591,132 A | 1/1997 | Carrie |
| 5,643,236 A | 7/1997 | Hadley |
| 5,653,700 A | 8/1997 | Byrne et al. |
| 5,681,274 A | 10/1997 | Perkins et al. |
| 5,690,645 A | 11/1997 | Van Erp |
| 5,713,851 A | 2/1998 | Boudewijn et al. |
| 5,715,815 A | 2/1998 | Lorenzen et al. |
| 5,745,926 A | 5/1998 | Cailleteau |
| 5,756,144 A | 5/1998 | Wolff et al. |
| 5,846,259 A | 12/1998 | Berthiaume |
| 5,863,287 A | 1/1999 | Segawa |
| 5,948,343 A | 9/1999 | Hiroki et al. |
| 5,951,929 A | 9/1999 | Wilson |
| 6,004,305 A | 12/1999 | Hursman et al. |
| 6,010,479 A | 1/2000 | Dimitri |
| 6,053,905 A | 4/2000 | Daignault, Jr. et al. |
| 6,059,107 A | 5/2000 | Nosted et al. |
| 6,063,063 A | 5/2000 | Harboe et al. |
| 6,090,075 A | 7/2000 | House |
| 6,149,996 A | 11/2000 | Helgerson et al. |
| 6,158,912 A | 12/2000 | Miraglia et al. |
| 6,217,569 B1 | 4/2001 | Fiore |
| 6,245,047 B1 | 6/2001 | Feda et al. |
| 6,257,463 B1 * | 7/2001 | De Polo ............ B65D 47/243 222/525 |
| 6,355,004 B1 | 3/2002 | Pedersen et al. |
| 6,409,717 B1 | 6/2002 | Israelsson et al. |
| 6,524,926 B1 | 2/2003 | Allman et al. |
| 6,578,709 B1 | 6/2003 | Kavanagh et al. |
| 6,602,244 B2 | 8/2003 | Kavanagh et al. |
| 6,634,498 B2 | 10/2003 | Kayerod et al. |
| 6,786,884 B1 | 9/2004 | DeCant, Jr. et al. |
| 6,849,070 B1 | 2/2005 | Hansen et al. |
| 6,902,146 B1 * | 6/2005 | Elliott ............... A61F 5/4556 251/351 |
| 6,911,016 B2 | 6/2005 | Balzum et al. |
| 7,311,698 B2 | 12/2007 | Tanghoj et al. |
| 7,380,658 B2 | 6/2008 | Murray et al. |
| 7,517,343 B2 | 4/2009 | Tanghoej et al. |
| 7,682,353 B2 | 3/2010 | Tanghoj et al. |
| 7,922,712 B2 | 4/2011 | Tanghoj et al. |
| 8,002,766 B2 | 8/2011 | Tanghoej et al. |
| 8,282,624 B2 | 10/2012 | Tanghoej et al. |
| 8,529,549 B2 | 9/2013 | Tanghoej et al. |
| 8,679,092 B2 | 3/2014 | Tanghoej et al. |

(56) References Cited

U.S. PATENT DOCUMENTS

| | | | |
|---|---|---|---|
| 2001/0001443 A1* | 5/2001 | Kayerod | A61L 29/085 206/364 |
| 2002/0103467 A1 | 8/2002 | Kubalak | |
| 2002/0156458 A1* | 10/2002 | Latour, Jr. | A61F 2/0009 604/517 |
| 2003/0004496 A1 | 1/2003 | Tanghoj | |
| 2003/0018293 A1 | 1/2003 | Tanghoj et al. | |
| 2003/0018302 A1 | 1/2003 | Kavanagh et al. | |
| 2003/0018322 A1 | 1/2003 | Tanghoj et al. | |
| 2003/0060807 A1* | 3/2003 | Tanghoj | A61M 25/0017 604/544 |
| 2004/0153051 A1 | 8/2004 | Israelsson et al. | |
| 2004/0158231 A1 | 8/2004 | Tanghoj et al. | |
| 2004/0163980 A1 | 8/2004 | Tanghoj et al. | |
| 2004/0236293 A1 | 11/2004 | Tanghoj et al. | |
| 2004/0254562 A1 | 12/2004 | Tanghoj et al. | |
| 2005/0043715 A1 | 2/2005 | Nestenborg et al. | |
| 2006/0025753 A1 | 2/2006 | Kubalak et al. | |
| 2006/0273119 A1* | 12/2006 | Lee | B65D 47/061 222/525 |
| 2008/0045921 A1 | 2/2008 | Anderson et al. | |
| 2008/0119803 A1* | 5/2008 | Lund | A61F 5/4404 604/327 |
| 2008/0260576 A1* | 10/2008 | Bruun | A61M 25/002 422/28 |
| 2009/0054876 A1* | 2/2009 | Borodulin | A61M 25/0017 604/544 |
| 2009/0137985 A1 | 5/2009 | Tanghoej et al. | |
| 2011/0197989 A1* | 8/2011 | Proulx | A61M 39/10 141/1 |
| 2011/0224653 A1 | 9/2011 | Torstensen | |
| 2012/0110951 A1* | 5/2012 | van Groningen | A61M 25/0111 53/425 |
| 2014/0148795 A1 | 5/2014 | Tanghoej et al. | |

FOREIGN PATENT DOCUMENTS

| | | |
|---|---|---|
| EP | 0086573 B1 | 8/1983 |
| EP | 0206558 A1 | 12/1986 |
| EP | 0336984 B1 | 10/1989 |
| EP | 0471429 B1 | 2/1992 |
| EP | 0495263 B1 | 7/1992 |
| EP | 0570370 B1 | 11/1993 |
| EP | 0658488 A1 | 6/1995 |
| EP | 0807447 B1 | 11/1997 |
| EP | 0824930 A2 | 2/1998 |
| EP | 0923390 B1 | 6/1999 |
| EP | 0923398 B1 | 6/1999 |
| EP | 0925802 A2 | 6/1999 |
| EP | 0958911 B1 | 11/1999 |
| EP | 0959930 B1 | 12/1999 |
| EP | 0980892 A1 | 2/2000 |
| EP | 1023882 A1 | 8/2000 |
| EP | 1034811 A1 | 9/2000 |
| EP | 1066069 A1 | 1/2001 |
| EP | 1116567 B1 | 7/2001 |
| EP | 1406690 B1 | 4/2004 |
| FR | 2293948 A1 | 7/1976 |
| GB | 1482873 A | 8/1977 |
| GB | 1493257 A | 11/1977 |
| GB | 1524704 A | 9/1978 |
| GB | 1598843 A | 9/1981 |
| GB | 2193485 A | 2/1988 |
| GB | 2231801 A | 11/1990 |
| GB | 2278285 A | 11/1994 |
| GB | 2230702 A | 4/1999 |
| GB | 2336830 A | 11/1999 |
| HU | 187406 A | 5/1984 |
| HU | 189812 B | 3/1985 |
| HU | 213805 B | 12/1993 |
| HU | 210728 B | 2/1994 |
| HU | 263 | 4/1994 |
| HU | 215792 B | 1/1995 |
| HU | 217867 B | 5/1996 |
| HU | 219512 B | 6/1997 |
| HU | 219423 B | 6/1998 |
| HU | 220326 B | 3/1999 |
| HU | 222366 B1 | 12/1999 |
| HU | 9903763 A2 | 3/2000 |
| HU | 223145 B1 | 12/2000 |
| HU | 201498 A2 | 9/2002 |
| JP | 5135585 A | 3/1976 |
| JP | 6257352 B2 | 11/1987 |
| JP | 6429271 A | 1/1989 |
| JP | 223556 U | 2/1990 |
| JP | 294559 Y2 | 7/1990 |
| JP | 3112618 B2 | 5/1991 |
| JP | 4218168 A | 8/1992 |
| JP | 7501232 A | 2/1995 |
| JP | 852218 A | 2/1996 |
| JP | 9123212 A | 5/1997 |
| JP | 11115038 A | 4/1999 |
| JP | 11507283 A | 6/1999 |
| JP | 2929617 B2 | 8/1999 |
| JP | 11347129 A | 12/1999 |
| SE | 505615 C2 | 7/1994 |
| SE | 518002 C2 | 4/1999 |
| WO | WO8902763 A1 | 4/1989 |
| WO | WO9000960 A1 | 2/1990 |
| WO | WO9105577 A1 | 5/1991 |
| WO | WO9118640 A1 | 12/1991 |
| WO | WO9207607 A1 | 5/1992 |
| WO | WO9213718 A1 | 8/1992 |
| WO | WO9218310 A1 | 10/1992 |
| WO | WO9301855 A2 | 2/1993 |
| WO | WO9304723 A1 | 3/1993 |
| WO | WO9319717 A1 | 10/1993 |
| WO | WO9408653 A1 | 4/1994 |
| WO | WO9524235 A1 | 9/1995 |
| WO | WO9619254 A1 | 6/1996 |
| WO | WO9630277 A1 | 10/1996 |
| WO | WO9640345 A1 | 12/1996 |
| WO | WO9641653 A1 | 12/1996 |
| WO | WO9707707 A1 | 3/1997 |
| WO | WO9726937 A1 | 7/1997 |
| WO | WO9747349 A1 | 12/1997 |
| WO | WO9806642 A1 | 2/1998 |
| WO | WO9811932 A1 | 3/1998 |
| WO | WO9819729 A1 | 5/1998 |
| WO | WO9858988 A1 | 12/1998 |
| WO | WO9858989 A1 | 12/1998 |
| WO | WO9858990 A1 | 12/1998 |
| WO | WO9923978 A1 | 5/1999 |
| WO | WO9930761 A1 | 6/1999 |
| WO | WO9942155 A2 | 8/1999 |
| WO | WO0016843 A1 | 3/2000 |
| WO | WO0030575 A1 | 6/2000 |
| WO | WO0132240 A1 | 10/2001 |
| WO | WO03008029 A2 | 1/2003 |
| WO | 2004089454 A1 | 10/2004 |
| WO | 2006005349 A2 | 1/2006 |

OTHER PUBLICATIONS

Brochure entitled "Clear Injection Molding", downloaded from www.coloritepolymers.com/product/clear.sub.—injection.sub.—moulding.html on Mar. 8, 2010 (2 pages).

Brochure entitled "Hinweise zum katheterisieren mit LoFric", Astra Tech GmbH, Limburg 1996 (Google translation: Information for catheterize with LoFric).

Brochure entitled "LoFric Patientenratgeber", Astra Tech GmbH, 1996 (Google translation: patient-counselor).

Eckmann, David M., "Variations in Epidural Catheter Manufacture: Implications for Bending and Stiffness", Regional Anaesthesia and Pain Medicine, vol. 28, No. 1 (Jan.-Feb.), 2003, pp. 37-42.

European Search Report issued in EP application No. 05023729.6, dated Dec. 1, 2010.

European Search Report issued in EP Application No. 08173110, dated Feb. 19, 2009.

European Search Report issued in EP Application No. 10180784, dated Oct. 14, 2010.

(56) References Cited

OTHER PUBLICATIONS

Grounds of Appeal filed in EP Application No. 02754547, issued as Patent No. 1420845, filed by Astra Tech AB, dated Nov. 9, 2010.
International Search Report issued in PCT/DK02/00449 mailed Jul. 4, 2003, 4 pages.
Notice of Opposition filed in EP application No. 02748637.2 by Astra Tech AB, Mar. 10, 2010.
Notice of Opposition filed in EP application No. 02748637.2 by Hollister Inc., Mar. 10, 2010.
Office Action issued in AU Application No. 2008201719, May 7, 2010, 3 pages.
Office Action issued in CA Application No. 2,451,356, Nov. 5, 2009.
Office Action issued in CA Application No. 2,451,364, Jul. 6, 2009.
Office Action issued in EP Application No. 02748636 dated Apr. 30, 2007.
Office Action issued in EP Application No. 02748637 dated Mar. 29, 2007.
Office Action issued in JP Application No. 2003-508417, Sep. 29, 2009, (Translation).
Office Action issued in JP Application No. 2003-508539, Sep. 29, 2009 (Translation).
Office Action issued in U.S. Appl. No. 12/698,241, Mar. 31, 2011.
Office Action issued in U.S. Appl. No. 13/078,012, May 13, 2013.
Report of Pretrial Examination (Translation) issued in JP Appeal Trial No. 2010-002073, JP Application No. 2003-508539, Jun. 3, 2010, 2 pages.
Stenqvist, O. et al., "Stiffness of Central Venous Catheters", Acta Anaesthesiol Scand 1983: 27: 153-157.

\* cited by examiner

CATHETER ACTIVATION BY HANDLE REMOVAL

The invention relates to a catheter kit comprising a catheter and a urine bag stored in a package wherein flow is prevented between the catheter and urine bag when stored but enabled when the kit is used.

BACKGROUND

Catheter packages exist in which a hydrophilic coated catheter is stored in liquid swelling medium. When such a catheter package is combined with a urine collecting bag into a catheter kit, it is undesirable that the swelling medium enters the bag. This makes it uncertain how large an amount is present in the container for wetting catheter. If there is not enough swelling medium present then the catheter may dry out. Furthermore, swelling medium often evaporates into a crystalline structure which may clog the construction, thereby preventing liquid from flowing through the catheter and into the bag. Finally, swelling medium in the urine bag is perceived unhygienic, and for a user where hygiene is important such perception may deter him from using the product.

Thus, there exists a need for a catheter kit as described where it is prevented that liquid flows from the catheter and into the urine bag before use of the catheter kit.

DESCRIPTION OF RELATED ART

WO9811932 discloses a urinary catheter assembly comprising a urinary catheter having on at least a part of its surface a hydrophilic surface layer intended to produce a low-friction surface character of the catheter by treatment with a liquid swelling medium prior to use of the catheter and a catheter package having a cavity for accommodation of the catheter.

DESCRIPTION OF THE INVENTION

Claim 1

The invention relates to a catheter kit comprising a urinary catheter, a urine collecting bag and a container, the urinary catheter having a hydrophilic coating and comprising a tubular element having a proximal end and a distal end, the proximal end being provided with eyelets for letting urine enter into the urinary catheter, the distal end being provided with a handle for handling the catheter, the urine collecting bag being connected to the handle, the container being adapted for storing the catheter and for containing a liquid swelling medium for wetting the hydrophilic coating on the catheter, the catheter kit further comprises a cover detachably attached to the container for covering the catheter handle and the urine collecting bag, the catheter kit further comprises sealing means, wherein
  in the sealing configuration flow is prevented between the catheter and the urine bag, and
  in the flow configuration flow is possible between the catheter and the urine bag.

The invention relates to a catheter kit comprising a container with a urinary catheter connected to a urine collecting bag. When the catheter kit is in the sealing configuration—typically when stored, or just prior to use—then the liquid swelling medium in the container is prevented from entering into the urine collecting bag. When the catheter kit is in the flow configuration—typically when the kit is ready to be used—the urine is capable of flowing into the catheter through the eyelets and out through an outlet opening provided in the handle and into the urine collecting bag. In the flow configuration, the urinary catheter including the handle and the urine collecting bag is removed from the container.

The typical transformation from the sealing configuration to the flow configuration will happen as the user prepares the catheter kit from storing to use. When the catheter kit is stored, the cover is attached to the container and the catheter is stored in the container, the handle and the urine collecting bag also being covered by the container and/or cover. When the user intends to use the product, initially the cover is removed from the container and the urinary catheter including the urine collecting bag is removed from the container, typically by gripping the handle of the catheter. The removal of the urinary catheter from the container may de-activate sealing means in the handle or between the cover and the handle and thus transform the catheter kit from the sealing configuration to the flow configuration. Thus, in one embodiment, sealing means is provided in the handle or between the cover and the handle. Alternatively, the user has to remove or de-activate sealing means at the inlet to the urine collecting bag, thus in the alternative embodiment, the sealing means is provided at an inlet to the urine collecting bag. The inlet to the urine collecting bag is defined as the transition between the handle and the urine collecting bag.

In the following, whenever referring to the proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted.

The longitudinal direction is the direction from the distal to the proximal end. The transverse direction is the direction perpendicular to the longitudinal direction, which corresponds to the direction across the shaft or tubular element of the catheter.

The catheter described in this application may be used as a urinary catheter.

The catheter comprises a generally tubular element extending from the distal end to the proximal end. The tip is positioned in the proximal end of the catheter and may be provided as a rounded closed end of the tube constituting the main part of the catheter. The connector is provided in the distal end and may in an embodiment comprise a flared end of the catheter, so that the diameter of the connector increases with respect to the remaining tubular element.

Usually catheters used as urinary draining devices are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus, 8 FR corresponds to a catheter with an outer diameter of 2.7 mm and 18 FR corresponds to a catheter with an outer diameter of 6 mm.

Catheters of this invention are prior to use provided with a hydrophilic coating so as to impart a low-friction insertion.

The catheter may be a telescopic compact catheter for example as SpeediCath® Compact Female or Male marketed by Coloplast A/S.

In one embodiment the handle is coupled to the container. Preferably, it is coupled by a liquid tight coupling, so that the swelling medium is prevented from exiting the container. Thus, the liquid tight coupling should be able to contain the liquid swelling medium inside the container for the storage period, which may be up to 3-5 years. When the handle and thereby also the catheter are removed from the container, liquid flow is established between the catheter and the urine bag.

In an embodiment the catheter kit is moved from the sealing configuration to the flow configuration by axially displacing the urinary catheter and the handle relative to each other. This allows for flow to be established between the handle and the urinary catheter when the handle is pulled, unscrewed or otherwise axially displaced with respect to the urinary catheter. This type of seal provides for a particular secure sealing that will not inadvertently be activated.

In a related embodiment, the axial displacement occurs as a result of pulling the handle in the axial direction. In this case, the coupling between the handle and the catheter may be provided as a snap fit coupling.

In another related embodiment, the axial displacement occurs as a result of rotating the handle with respect to the urinary catheter. In the latter embodiment, the coupling between the handle and the urinary catheter may as an example be provided as a threaded coupling with a large pitch ratio.

In another embodiment, the catheter kit is moved from the sealing configuration to the flow configuration by rotationally displacing the urinary catheter and the handle relative to each other. This allows for flow between the handle and the catheter to be established by turning the handle.

In a related embodiment a first sealing disc is provided in the proximal end of the handle and a second sealing disc in the distal end of the catheter. The sealing discs are coaxially aligned and are arranged in tight engagement.

The rotatable connection between the handle and the catheter results in the fact that the sealing discs are able to rotate relative to each other.

At least one flow opening is provided in each sealing disc. The flow openings are provided so that they may be aligned in one rotatable position between the handle and the catheter and thereby flow is allowed to pass from the catheter and into the urine bag, and in another position where the flow openings are out of alignment flow is closed off (or prevented) between the catheter and the urine bag.

In other embodiments, the kit is moved from the sealing configuration to the flow configuration by removing the cover.

As an example, the cover may provide a seal against the distal end of the handle when the catheter kit is in its sealing configuration. Alternatively, a valve can be arranged between the cover and the handle of the catheter and wherein the valve is opened and the kit is moved from the sealing configuration to the flow configuration when the cover is removed.

Other embodiments relate to providing a sealing element providing a liquid tight seal at the distal end of the handle, corresponding to the inlet to urine collecting bag. This sealing element seals the catheter kit when the kit is in the sealing configuration and allows for flow through the catheter and into the urine collecting bag when the kit is in the flow configuration.

In yet other embodiments, the kit can be moved from the sealing configuration to the flow configuration by directly removing a sealing element which provides a liquid tight seal and is arranged at the inlet to the urine collecting bag.

Alternatively, the seal can be broken by e.g. twisting, squeezing or otherwise handling of the sealing element by the user.

In one embodiment, the handle is rotatable connected to the container. The handle is provided with an external thread for threaded engagement with a corresponding thread on the container.

If the handle is capable of rotating with respect to the catheter and at the same time the handle is rotatable connected to the container, an embodiment may be achieved that is particularly easy to use. In such an embodiment, the user only has to rotate the handle and will with this rotation firstly open for the flow (transform the catheter kit from the sealing configuration to the flow configuration) and secondly remove the urinary catheter and urine collecting bag from the container. Thus, the user will hold the container with one hand (or between the elbow and the body or in any other way) and the handle with the other hand (or use the teeth or in any other way) and rotate the two parts with respect to each other.

DETAILED DESCRIPTION OF THE DRAWING

FIGS. 1-4 show in a stepwise sequence a catheter kit 1 and how the catheter is prepared for use. The different embodiments disclosed herein may be incorporated into the catheter kit 1 by a person skilled in the art.

Figure 1:
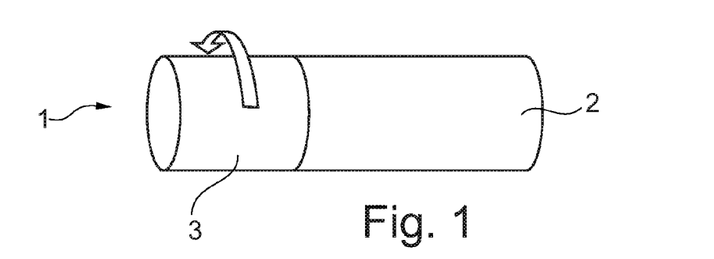
FIGS. 1-4 show one embodiment of a catheter kit, wherein flow can be controlled.
Figure 2:
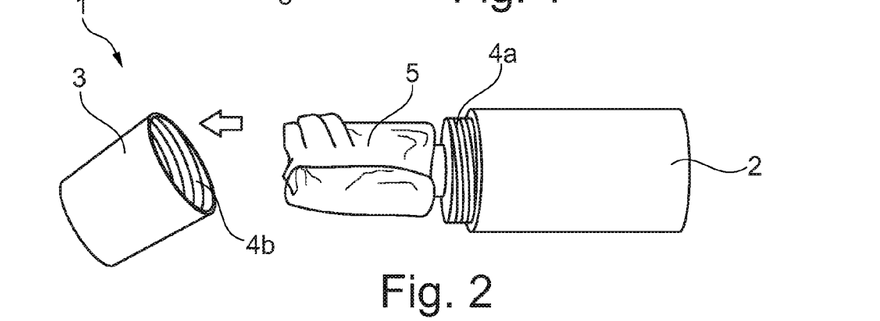

The catheter kit comprises a container 2 and a cover 3 for closing off and covering an opening of the container. The cover is removed by twisting the cover around along the arrow as shown in FIG. 1. This releases the cover from the threaded coupling 4a, 4b as shown in FIG. 2, which exposes a urine bag 5 which has been folded inside the cover 3. The cover may be discarded or saved for later re-closing of the catheter kit 1.

Figure 3:
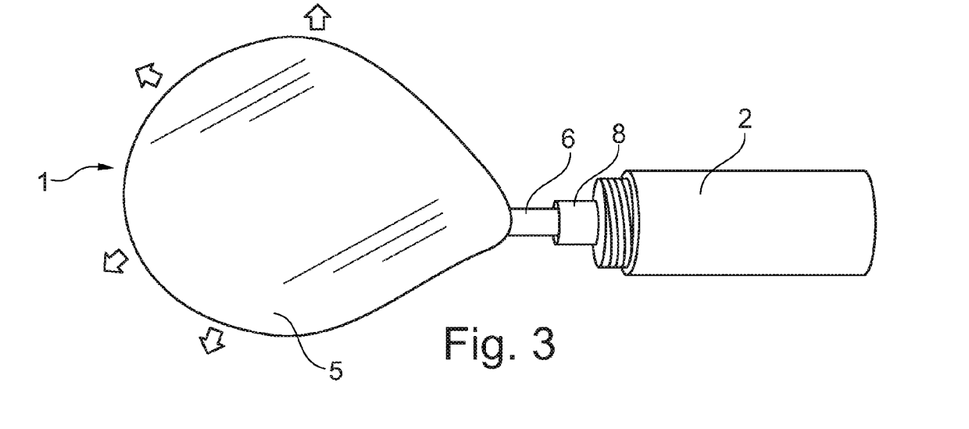

The urine bag 5 is unfolded exposing a catheter handle 6 around which it were folded as seen in FIG. 3. The handle is attached to the distal end of a catheter 7. The handle is coupled with a neck portion 8 of container, which defines an opening of the container through which the catheter can be inserted and retrieved.

Figure 4:
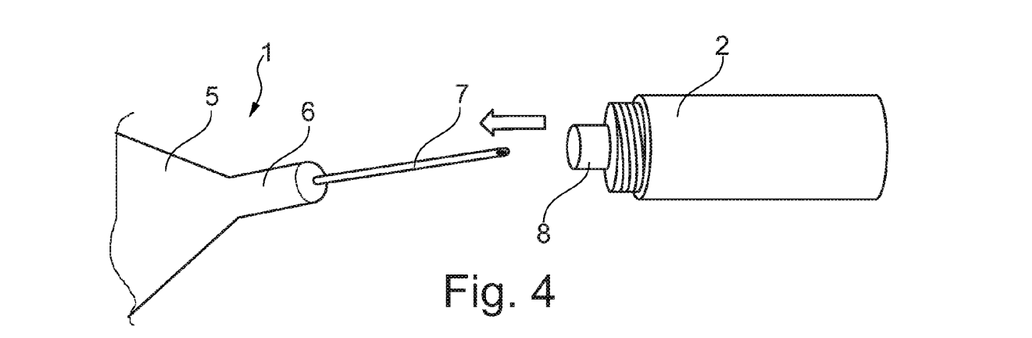

Finally, the catheter 7 and the urine bag 5 are removed from the container by pulling the handle 6 as shown in FIG. 4, whereby the catheter is ready for insertion into the urethra.

The catheter is hydrophilic coated and stored together with a swelling medium (not shown) in the container.

As will be understood, the catheter may be coupled to the container in different ways. In one embodiment there may be a threaded coupling between the container and the catheter handle, or in another embodiment the coupling may for example be a frictional coupling. It is however preferred that the coupling is liquid tight so that swelling medium does not leak from the container.

Figure 5:
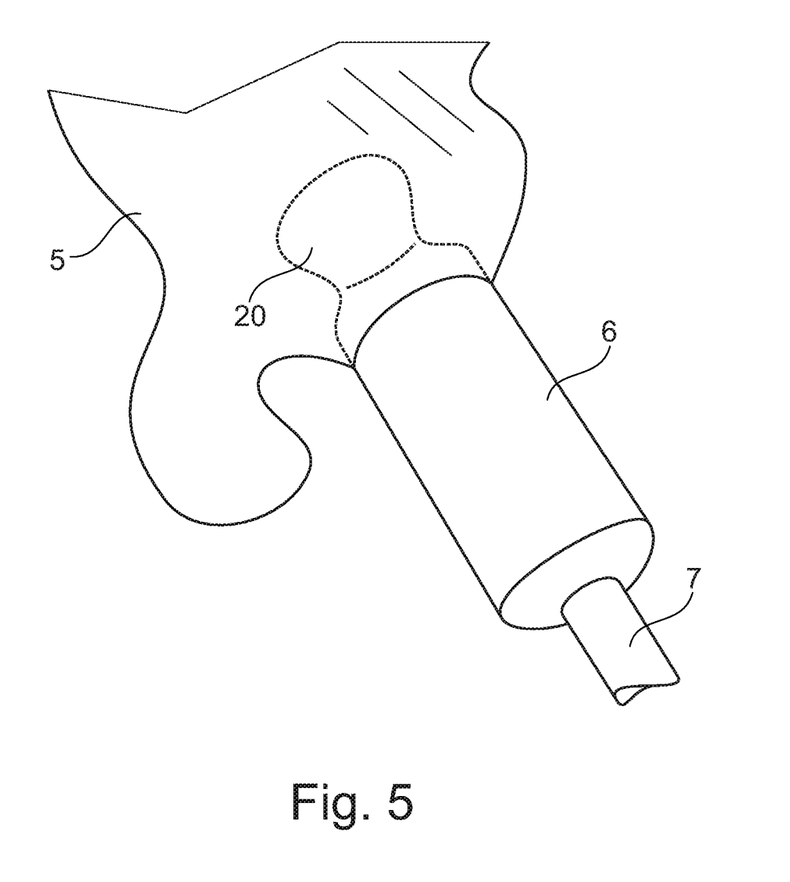
FIG. 5 shows an embodiment of a seal between the catheter and the urine bag.

FIG. 5 illustrates a break off part 20 formed on the distal end of the handle, i.e. the end opposite the catheter 7. In order to move the catheter kit from the sealing configuration to the flow configuration the break off part 20 is broken off manually by the user. By providing the break off part 20 within the urine bag it will stay therein and not fall on the ground and litter.

Other closure means, which has to be separately manually removed in order to move the catheter kit in to the flow configuration may be provided. In one embodiment, such manual means may for example be a clamp arranged around the bag close to distal end of the handle, a string or rubber band. These are means which are easy to identify and thus easy for the user to remove.

In another set of embodiments, the catheter kit can be moved from a sealing configuration to a flow configuration by manipulating the handle as described in FIGS. 6-13. This has the advantage that the catheter kit can be moved into the flow configuration when the catheter is removed from the container and thus it can be incorporated into the removal step, whereby the user will not have to perform additional operations.

Figure 6:
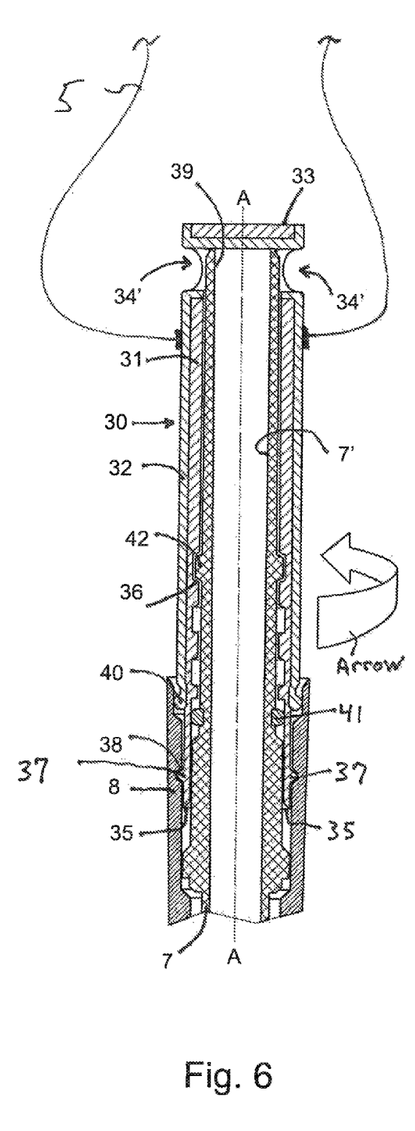
FIGS. 6 and 7 show an embodiment of a sealing configuration that are opened by removing the catheter from the container.
Figure 7:
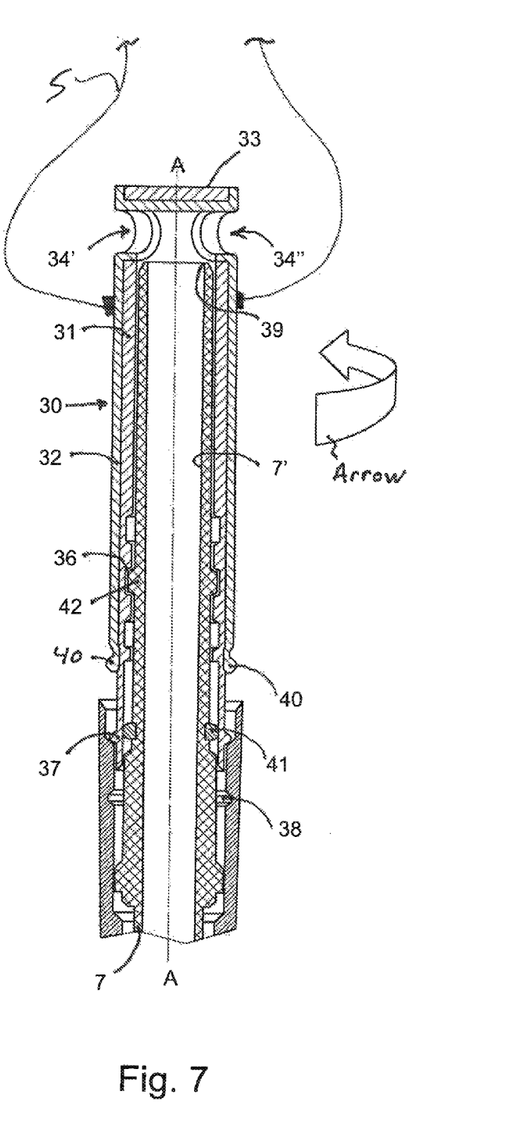
Figures 8, 9, 10:
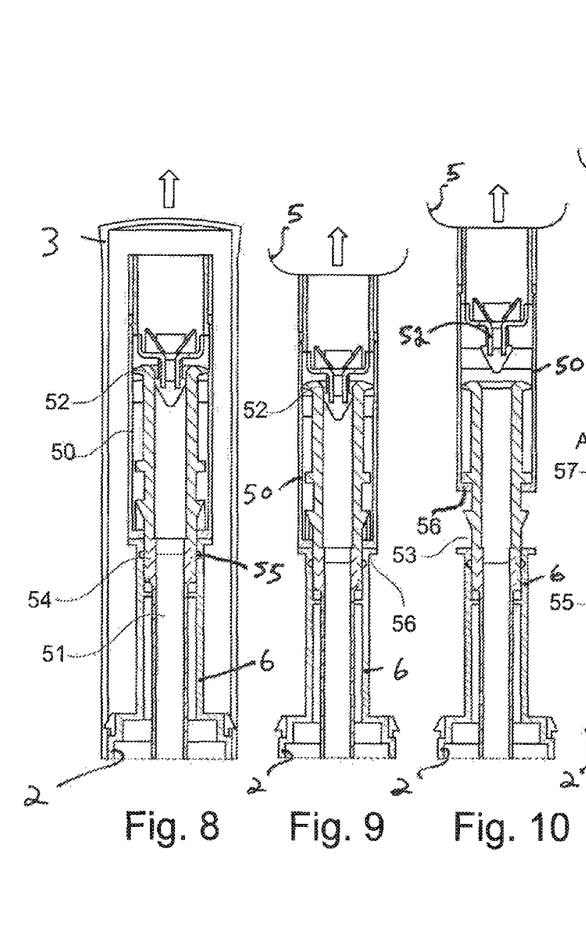
FIGS. 8-12 show another embodiment of a sealing configuration that are opened by removing the catheter from the container.
Figures 11, 12:
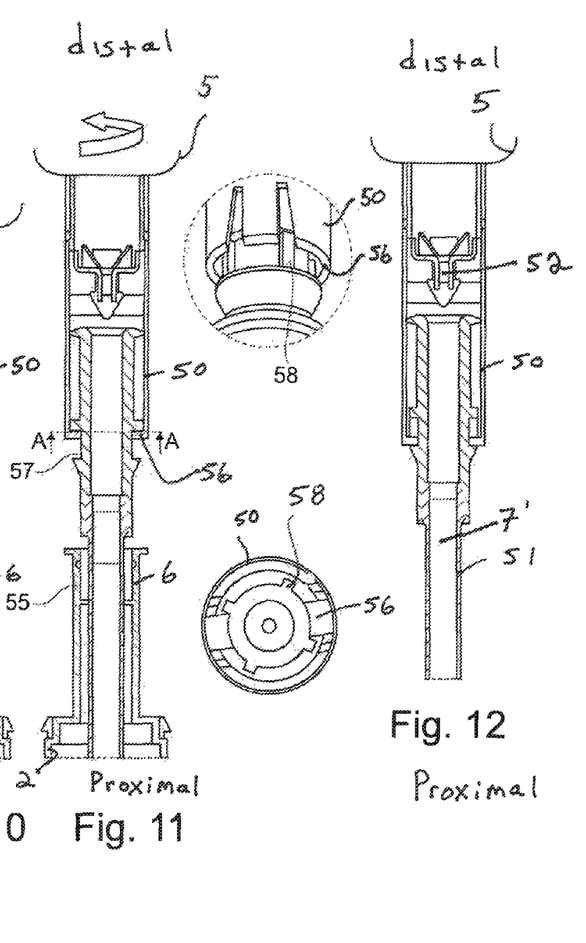

FIGS. 6 and 7 illustrate a handle 30 having a double threaded coupling structure which serves to first move the catheter kit into the flow configuration and second to separate the handle and the catheter from the container neck 8.

The handle is formed of a rigid inner tubular part 31 which is covered with a soft rubber layer 32. The rubber layer provides a gripping area which is comfortable to grip and have good gripping characteristics such as high friction.

The handle extends longitudinal along axis A-A, which corresponds to the longitudinal axis of the catheter. At a distal end 33 the handle has two outlet opening 34', 34". The catheter extends out from the proximal end 35 of the handle.

The handle is formed with an inner thread 36 provide on the inner surface of the tubular part 31. The inner thread engages with a corresponding catheter thread 42 provided on the outer surface of the distal end of the catheter 7.

An outer thread 37 is furthermore provided at proximal end of the handle on the outer surface of the tubular part. The outer thread engages with a corresponding container thread 38 provided on the inner surface of the neck 8 of the container.

In the sealed configuration the distal end 39 of the catheter closes off the passage to the outlet openings 34', 34", so that flow is prevented from the catheter lumen 7' and into the urine bag 5.

When the catheter kit is opened the handle is turned around the longitudinal axis A-A relative to the container as indicated by the arrow. This activates the threaded coupling between the handle and the catheter shifting the handle axially relative to the catheter, thereby shifting the distal end 39 of the catheter away from the outlet openings 34', 34" as shown in FIG. 7 allowing urine to flow through the catheter and into the urine bag.

This action goes mainly unnoticed for the user, who is turning in order to retrieve the catheter for use. With the catheter kit in the flow configuration the user continues to turn whereby the threaded coupling between the outer surface of the handle 37 and the inner surface of the neck 38 is activated. This unscrews the handle and thereby the catheter out of the container.

In order to prevent leaks when the product is stored, an outer sealing ring 40 prevents liquid to leak out between the handle and the neck and an inner sealing ring 41 prevents liquid from leaking out between the handle and the catheter.

In another embodiment as shown in FIGS. 8-12 the handle 50 and thereby the catheter 51 is removed from the container 2 by a pull and turn action.

The handle comprises a plug 52 which is used to seal off the catheter lumen 7' in the distal end of the catheter. As long as the plug seals of the catheter, the handle is free to rotate around the catheter in the groove 53. This prevents that coupling means in the form of a catheter thread 54 on the outer surface of the catheter and a container thread 55 on the inner surface of the neck is activated.

When the handle is pulled in the longitudinal axis, the plug 52 is moved out of the catheter lumen 7', thereby establishing flow between the catheter and the urine bag. At the same time the rib 56 is moved from the groove 53 into the locking groove 57. In the locking groove the rib is prevented from free rotation by locking ribs 58. Thus, when the handle is turned the catheter thread 54 and the container thread 55 is activated and the handle can be unscrewed from the container releasing the catheter.

Figure 13A:
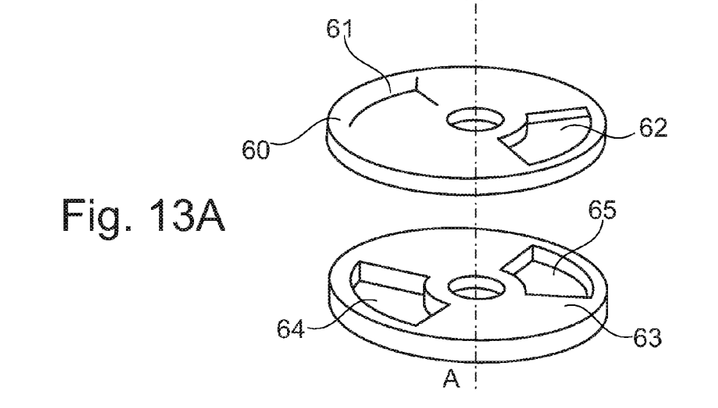
FIGS. 13a, 13b and 13c show the principles of yet other embodiments of sealing configurations that are opened by removing the catheter from the container.
Figure 13B:
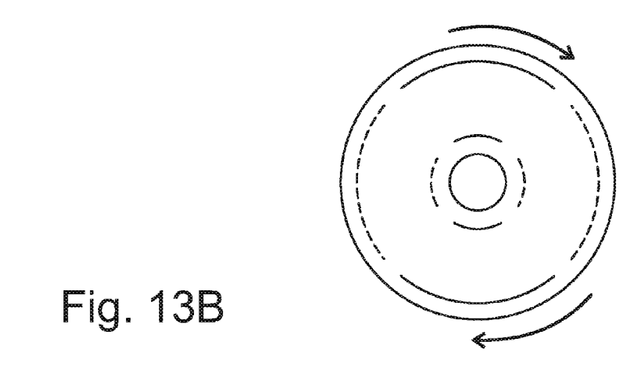
Figure 13C:
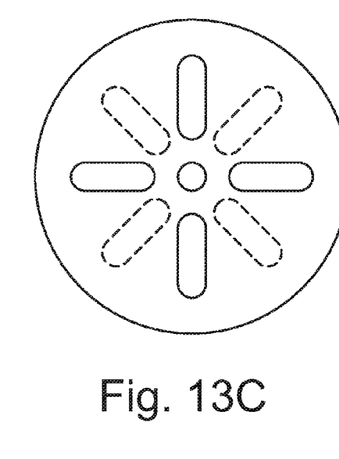

In FIGS. 13a, b and c it is in general illustrated how the catheter device may be moved to its flow configuration by rotation of two parts wherein openings are aligned.

For example, the proximal end of the catheter handle 6 can be provided with a handle disc 60 having two diametrically opposed openings 61, 62 and the distal end of the catheter 7 is provided with a catheter disc 63 also having two diametrically opposed openings 64, 65 similar to that of the handle disc.

The handle and the catheter are rotatable relative to each other which provide a rotation around axis A-A as shown in FIG. 13b. Thus, the openings can be moved into a flow configuration where the openings of the respective discs are aligned with each other and in the same manner the openings can be moved into a sealing configuration where the openings are displaced relative to each other thereby closing off flow.

FIG. 13c shows another embodiment of the discs described in respect to FIGS. 13a and 13b, where the openings are formed as slits. The principle and function of the slits and the discs are however the same as that of FIGS. 13a and 13b.

In another set of embodiments illustrated in FIGS. 14-17, the catheter kit is moved into its flow configuration as the cover is removed, as the removal simultaneous breaks a seal between the catheter lumen and the urine bag.

Figure 14:
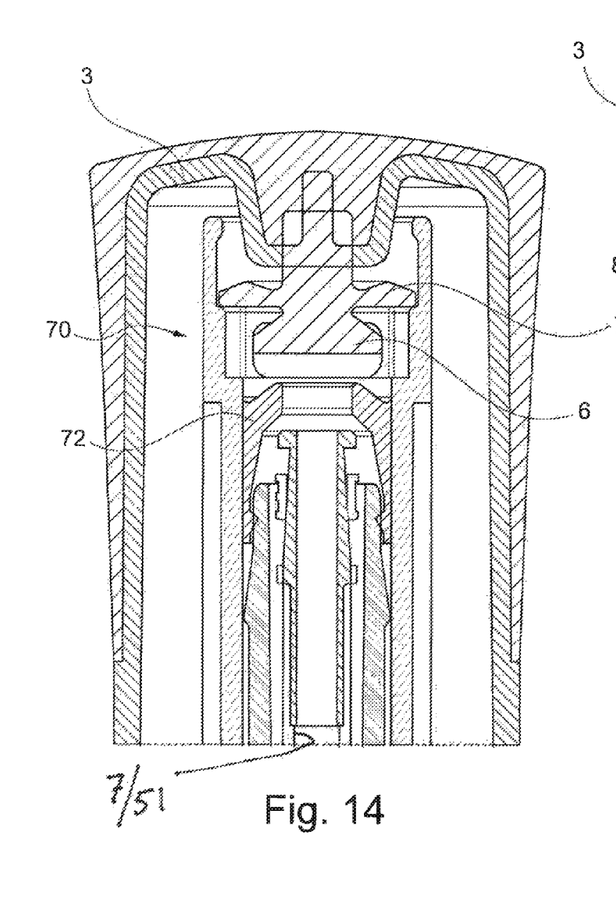
FIGS. 14, 15 and 16 show different embodiment of providing a seal between the catheter and the urine bag by using the cover as a retainer.

In FIG. 14 a seat valve 70 is provided between the cover 3 and the catheter handle 6. The seat valve comprises a valve component 71. The valve component 71 is pushed into engagement with the valve seat 72 by the cover 3. This engagement prevents liquid from flowing out of the handle 6. When the cover 3 is removed the seat valve relaxes and flow may be established.

Figure 15:
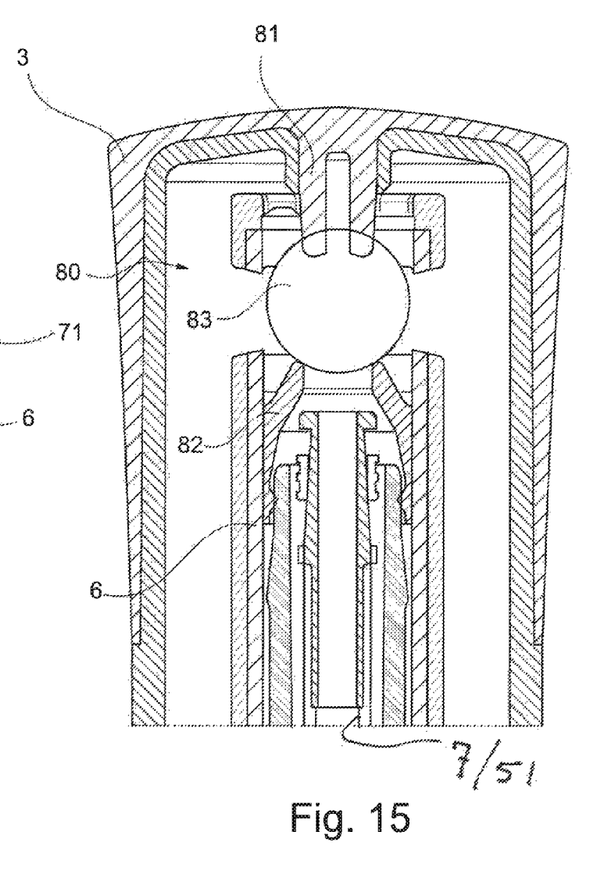

FIG. 15 shows a ball valve 80 provided between the cover 3 and the catheter handle 6. A cover valve seat 81 is provided on the inside of the cover and a handle valve seat 81 is provided on the handle 6. When closed a ball 83 engages with the cover and handle valve seal and closes off flow. When the cover is removed the ball valve relaxes and flow is established.

The embodiments of FIGS. 14 and 15 show valves having a separate loose part, e.g. in the shape of valve component 71 and ball 83. When the kit is opened the part will fall from the valve typically into the bag. This prevents the valve from reuse.

Figure 16:
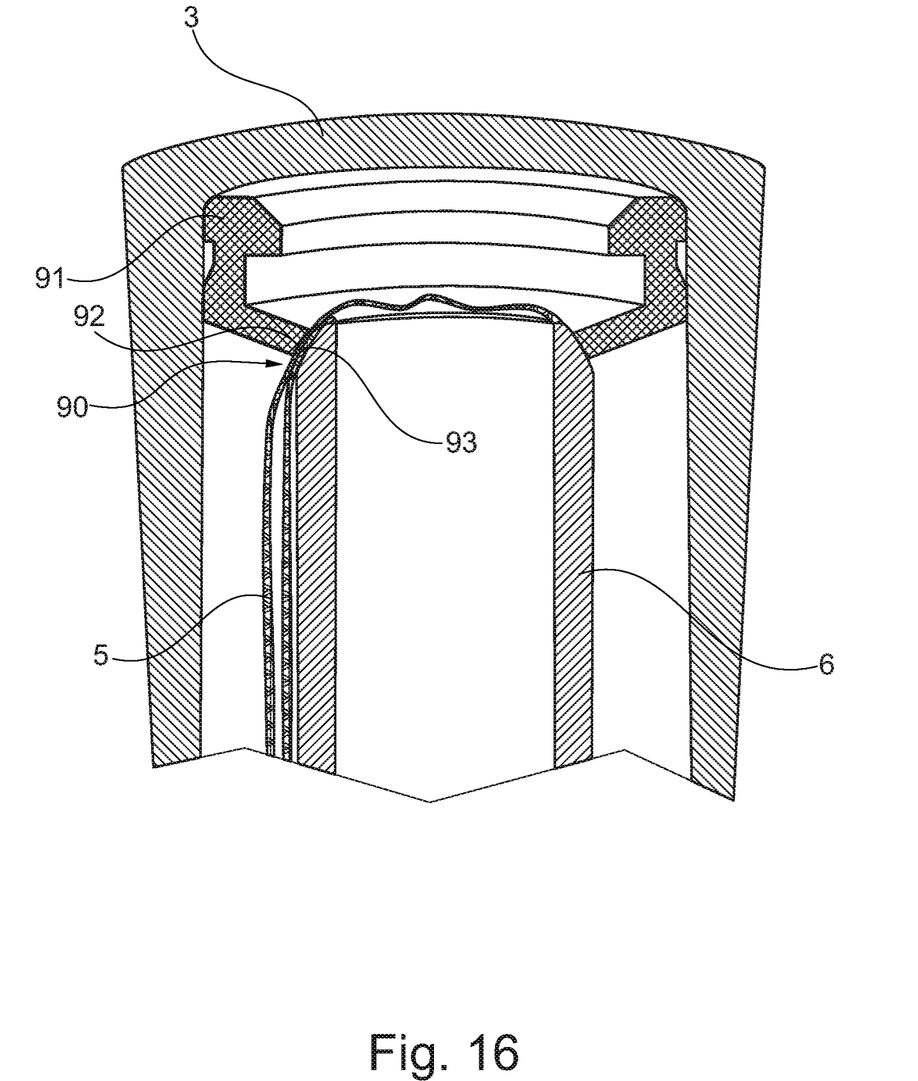

However, should it be desired to reuse the valve, an embodiment according to FIG. 16 can for example be used. FIG. 16 shows a valve construction 90 formed of an elastic valve seal 91 which is attached to the inside of the cover 3. The valve seal can for example be formed of a silicone or other elastomer. The valve seal 91 has a valve seat 92 which engages with a handle seat 93 on the distal part of the handle 6 when the kit is closed. The urine bag 5 which is attached to the handle extends out between the valve seat 92 and the handle seat 93. However, due to the pressure between the two seats the urine bag is pressed tight preventing liquid to flow pass the valve seal even through the urine bag. When the cover is removed the seal is broken and flow can be established. However, if the cover is put back on the valve set 92 will re-establish contact with the handle seat 93, thereby closing off flow.

In another embodiment, a foil is provided in the distal part of the handle and when the cover is twisted in order to remove it from the container a projecting pin cuts open at least part of the foil.

As has been described herein, many different ways of moving the catheter kit between a sealing configuration and a flow configuration have been disclosed, and the person skilled in the art will understand that many others can be employed within the scope of the present invention. For example principles such as kinking can also be used.

The invention claimed is:

1. A catheter kit comprising:
   a urinary catheter, a urine collecting bag and a container, the urinary catheter having a hydrophilic coating and comprising a tubular element having a proximal end provided with an eyelet sized to allow urine to enter into a lumen of the urinary catheter and a distal end connected to a handle, the urine collecting bag is connected to the handle and communicates with the lumen of the urinary catheter;
   wherein the container contains a liquid swelling medium in contact with at least the proximal end of the tubular element;
   wherein the catheter kit further comprises a cover attached to and separable from the container and seized to retain the catheter handle and the urine collecting bag with both of the urine collecting bag and the handle retained inside of the cover and outside of the container;
   wherein the handle comprises a plug inserted into the lumen of the urinary catheter
   to prevent flow of liquid between the urinary catheter and the urine collecting bag, and the plug is removable from the lumen of the urinary catheter to allow flow of liquid between the urinary catheter and the urine collecting bag.

2. The catheter kit according to claim 1, wherein the handle is coupled to the container in a liquid-tight coupling.

3. The catheter kit according to claim 1, wherein the plug is removable from the lumen of the urinary catheter by axial displacement of the urinary catheter relative to the handle.

4. The catheter kit according to claim 1, wherein the plug is removable from the lumen of the urinary catheter by axial displacement of the cover relative to the handle.

5. The catheter kit according to claim 1, wherein the plug is removable from the lumen of the urinary catheter by rotation of the handle with respect to the container.

6. The catheter kit according to claim 1, wherein the plug is removable from the lumen of the urinary catheter by rotationally displacing the urinary catheter and the handle relative to each other.

7. The catheter kit according to claim 1, wherein the handle is rotatably connected to the container by a threaded connection.

8. A compact and collapsible urinary catheter comprising:
   an intermittent urinary catheter having a tubular element with a lumen extending between an eyelet formed at a proximal end portion and a handle provided at a distal end portion of the tubular element, with the proximal end portion of the tubular element having a hydrophilic coating;
   a urine collecting bag connected to the handle and communicating with the lumen of the tubular element;
   a plug inserted into the lumen of the tubular element to prevent a flow of liquid from the intermittent urinary catheter into the urine collecting bag;
   a container containing at least the proximal end portion of the tubular element and a liquid swelling medium, with the proximal end portion of the tubular element in contact with the liquid swelling medium; and
   a cover secured to the container, with the urine collecting bag, the handle, and the plug located under the cover and outside of the container.

9. The compact and collapsible urinary catheter of claim 8, further comprising:
   a threaded connection between an outer surface of the handle and an inner surface of the container.

10. The compact and collapsible urinary catheter of claim 8, wherein the urine collecting bag is wrapped around the handle and stored inside of the cover.

11. The compact and collapsible urinary catheter of claim 8, wherein the urine collecting bag is wrapped around the handle and stored inside of the cover and outside of the container.

* * * * *